(12) United States Patent
Matsumoto et al.

(10) Patent No.: US 7,357,574 B2
(45) Date of Patent: Apr. 15, 2008

(54) RADIOGRAPHIC IMAGING APPARATUS

(75) Inventors: Kazuhiro Matsumoto, Saitama (JP); Hidero Matsumoto, Nishitokyo (JP); Osamu Tsujii, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 137 days.

(21) Appl. No.: 11/364,426

(22) Filed: Feb. 28, 2006

(65) Prior Publication Data

US 2006/0210021 A1 Sep. 21, 2006

(30) Foreign Application Priority Data

Mar. 16, 2005 (JP) ............................. 2005-075557

(51) Int. Cl.
*H05G 1/00* (2006.01)
(52) U.S. Cl. .................... 378/208; 378/37; 378/189
(58) Field of Classification Search ............. 378/37, 378/189, 208
See application file for complete search history.

(56) References Cited

U.S. PATENT DOCUMENTS

| | | | |
|---|---|---|---|
| 1,442,027 A | | 1/1923 | Levenson |
| 2,060,981 A | | 11/1936 | Fischer, et al. |
| 4,836,523 A | * | 6/1989 | Englander ..................... 5/623 |
| 5,036,530 A | | 7/1991 | DiGiovanna et al. |
| 5,090,044 A | | 2/1992 | Kobayashi |
| 5,386,447 A | * | 1/1995 | Siczek ........................ 378/37 |
| 5,600,702 A | | 2/1997 | Pigg |
| 5,742,962 A | * | 4/1998 | Yoshino et al. ................ 5/623 |
| 5,771,512 A | * | 6/1998 | Kurakake et al. ............. 5/623 |
| 5,820,552 A | * | 10/1998 | Crosby et al. ............ 600/407 |
| 6,419,390 B1 | * | 7/2002 | Landis-Lowell ........... 378/209 |
| 6,966,695 B2 | * | 11/2005 | Boomgaarden et al. ..... 378/177 |
| 2003/0084512 A1 | * | 5/2003 | Fujita et al. ................... 5/601 |
| 2006/0029181 A1 | | 2/2006 | Chen et al. |

FOREIGN PATENT DOCUMENTS

| | | |
|---|---|---|
| DE | 44 06 494 A1 | 8/1995 |
| FR | 2 847 461 | 5/2004 |
| GB | 2 038 150 A | 7/1980 |
| JP | A 05-042132 | 2/1993 |
| JP | A 2000-210280 | 8/2000 |
| JP | 2004-174019 | 6/2004 |

* cited by examiner

*Primary Examiner*—Edward J. Glick
*Assistant Examiner*—Thomas R. Artman
(74) *Attorney, Agent, or Firm*—Cowan, Liebowitz & Latman, P.C.

(57) ABSTRACT

A radiographic imaging apparatus which has an imaging system having a radiation source to irradiate a subject with radiation and a radiation detector to detect the radiation irradiated from the radiation source, and a radiographic imaging table to arrange the subject within the imaging system includes an arm holder which supports upward arms of the subject arranged on the radiographic imaging table, and a holder supporting member which supports the arm holder.

20 Claims, 17 Drawing Sheets

F I G. 10
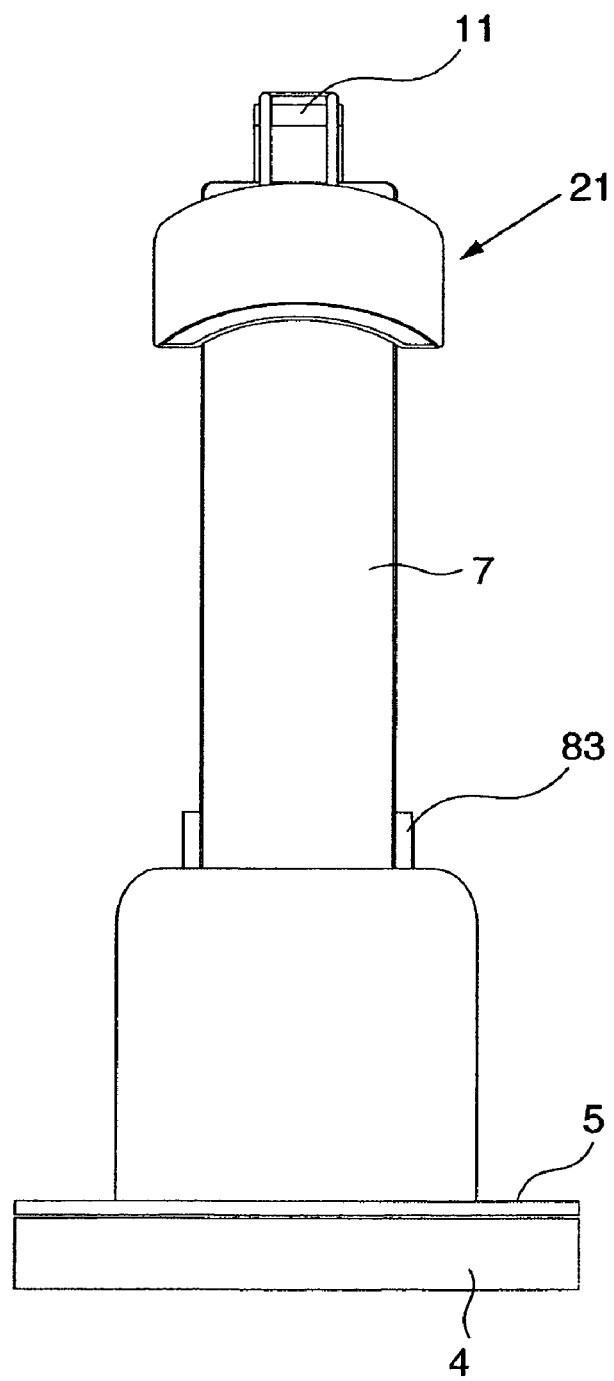

RADIOGRAPHIC IMAGING APPARATUS

FIELD OF THE INVENTION

The present invention relates to a radiographic imaging apparatus which takes a radiographic image of a subject while relatively rotating the subject and the imaging system, and a radiographic imaging table.

BACKGROUND OF THE INVENTION

A conventional radiographic imaging apparatus has an imaging system including a radiation tube to irradiate a subject with radiation and a radiation detector to detect the radiation. The radiation tube and detector are oppositely arranged such that a subject is sandwiched between them. A radiographic image of the subject is taken while relatively rotating the subject and imaging system. Conventionally known radiographic imaging apparatuses radiograph a subject in a standing or sitting position as well as in a side lying position (e.g., Japanese Patent Laid-Open Nos. 2000-210280 (p. 2, FIG. 1) and 5-42132 (p. 2, FIG. 1)).

The conventional standing or sitting type radiographic imaging apparatus which radiographs a subject in a standing or sitting position while rotating the subject or imaging system is not designed to place the arms of the subject by using an optimum means in radiographing the chest or belly of the subject. That is, the apparatus is unable to either avoid making a subject feel fatigue, pains, or fears during imaging or in changing or positioning the subject, or reliably maintain a condition with arms retracted from the imaging region during imaging. In addition, the apparatus has no good operability for a radiographer.

SUMMARY OF THE INVENTION

It is an exemplary object of the present invention to solve the above-described problems and provide a radiographic imaging apparatus and radiographic imaging table optimum for radiographing a subject in a standing or sitting position.

In order to achieve the above object, according to the present invention, there is provided a radiographic imaging apparatus comprising an imaging system having a radiation source to irradiate a subject with radiation and a radiation detector to detect the radiation irradiated from the radiation source; a radiographic imaging table to arrange the subject within the imaging system; an arm holder which supports upward arms of the subject arranged on the radiographic imaging table; and a holder supporting member which supports the arm holder.

According to the present invention, there is also provided a radiographic imaging table which arranges a subject within an imaging system including a radiation source to irradiate the subject with radiation and a radiation detector to detect the radiation irradiated from the radiation source, comprising an arm holder which supports arms of the subject upward; and a holder supporting member which supports the arm holder.

According to the present invention, during imaging or in changing or positioning a subject, the subject feels no fatigue, pains, or fears. During imaging, a condition with arms retracted from the imaging region can reliably be maintained. In addition, a radiographic imaging apparatus or radiographic imaging table having an arm holder with good operability for a radiographer can be provided.

Other objects and advantages besides those discussed above shall be apparent to those skilled in the art from the description of a preferred embodiment of the invention which follows. In the description, reference is made to accompanying drawings, which form a part hereof, and which illustrate an example of the invention. Such example, however, is not exhaustive of the various embodiments of the invention, and therefore reference is made to the claims which follow the description for determining the scope of the invention.

BRIEF DESCRIPTION OF THE DRAWINGS

FIG. 10 is a front view of the apparatus in FIG. 9;

DETAILED DESCRIPTION OF THE PREFERRED EMBODIMENTS

The embodiments of the present invention will be described below in detail with reference to the accompanying drawings. The embodiments to be described below are merely examples of means for implementing the present invention and should be changed or modified as needed in accordance with the configuration or various kinds of conditions of the apparatus to which the present invention is applied.

For example, an X-ray CT imaging apparatus will be described below as an application example of the present invention, which radiographs a subject by using X-rays and reconstructs a CT image. However, the present invention can also be applied to an imaging apparatus using another type of radiation or, e.g., an MRI apparatus other than the CT imaging apparatus.

First Embodiment

Figure 1:
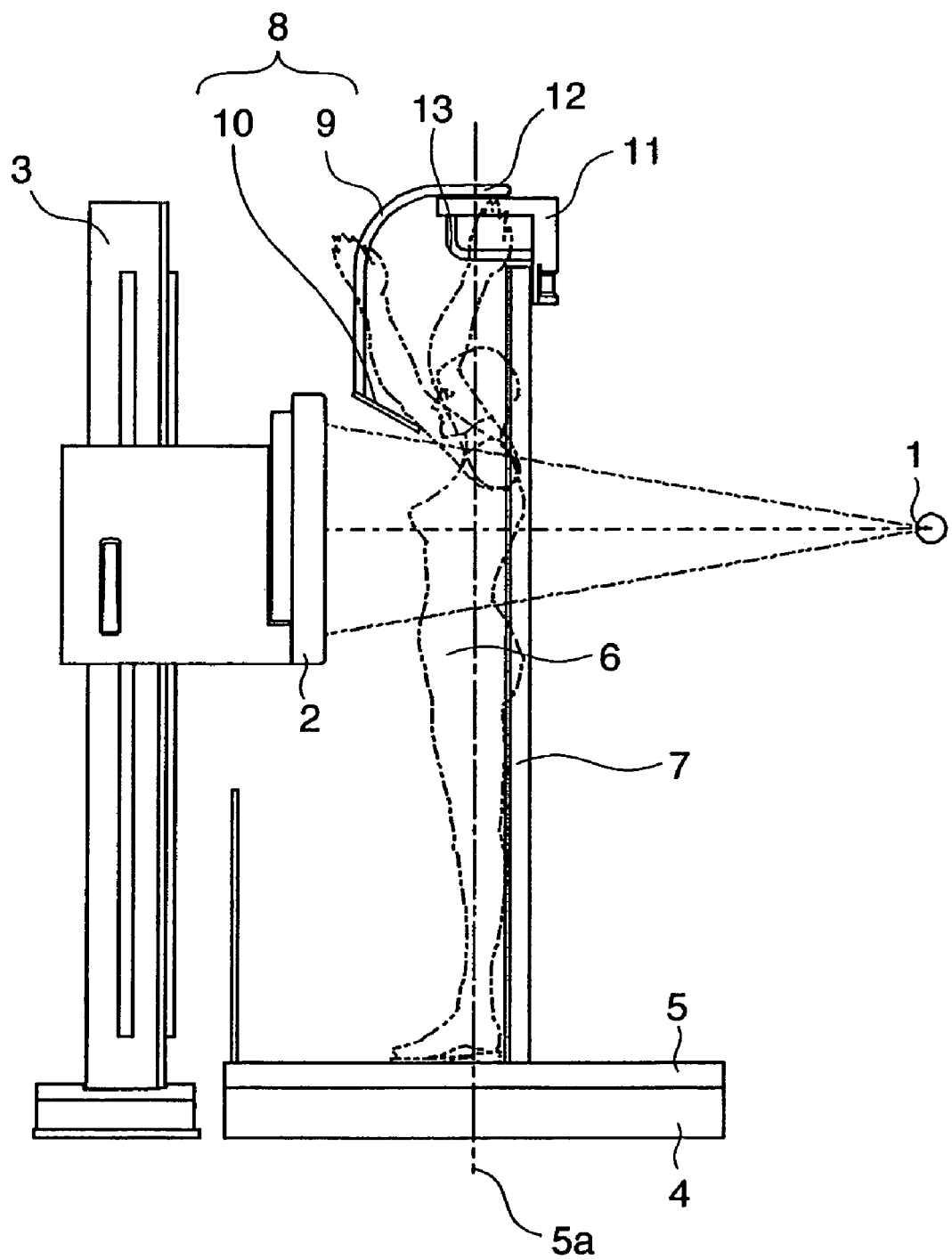
FIG. 1 is a side view showing the schematic arrangement of an X-ray CT imaging apparatus according to the first embodiment of the present invention.
Figure 2:
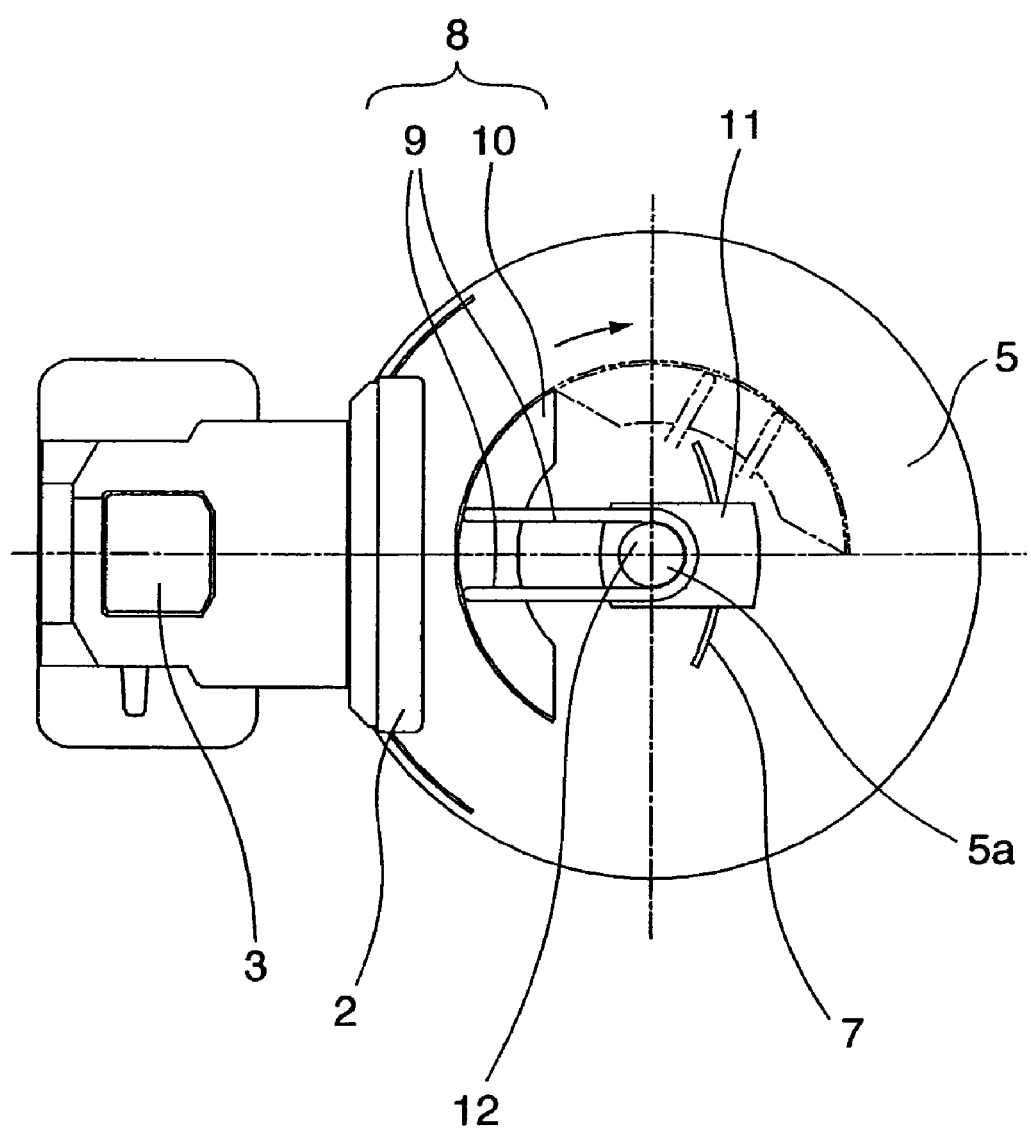
FIG. 2 is a plan view of the apparatus in FIG. 1.

FIG. 1 is a side view showing the schematic arrangement of an X-ray CT imaging apparatus according to the first embodiment of the present invention. FIG. 2 is a plan view of the apparatus in FIG. 1. The arrangement of the first embodiment will be described with reference to FIGS. 1 and 2.

The X-ray CT imaging apparatus of the first embodiment comprises an imaging system having an X-ray tube (radiation source) 1 to irradiate a subject as a patient with radiation and an X-ray detector 2 to detect X-rays (radiation) irradiated from the X-ray tube 1, and a medical X-ray imaging table to place the subject within the imaging system. A radiographic image of the subject is taken while relatively rotating the subject on the radiographic imaging table and the imaging system.

The X-ray tube 1 and 2D X-ray detector 2 are oppositely arranged. The X-ray tube 1 can be moved in the vertical direction by a moving mechanism (not shown). The 2D X-ray detector 2 includes a known scintillator (element which emits light in response to X-rays), a plurality of two-dimensionally arrayed photoelectric conversion elements (CCD or CMOS sensor), electric circuits, and a case. The X-ray detector 2 can detect an X-ray image. A supporting member 3 includes a post and guide members, which support and vertically move the X-ray detector 2 to place it at a desired level.

The radiographic imaging table has a subject supporting member 7 arranged between the X-ray tube 1 and the X-ray-detector 2. The subject supporting member 7 is connected to a turntable 5. A rotating table 4 can rotate the turntable 5 (in forward and reverse directions) about a rotation center 5a at a desired velocity by controlling a driving unit (not shown). The rotating table 4 has a detection mechanism (not shown) to detect the angle and speed of rotation of the turntable 5.

The subject supporting member 7 formed from a plate-shaped table supports the backside of a subject 6 in an upright position along its body axis, thereby placing the subject 6 near the rotation center 5a. The subject supporting member 7 is made of a material with high radiolucency (e.g., carbon fiber reinforced plastics) and curved in the widthwise direction.

An arm holder 8 to support the arms of the subject 6 from below faces the upper portion of the subject supporting member 7 with the rotation center 5a between. At this position, the X-ray detector 2 and arm holder 8 are spaced apart from each other by a predetermined distance so they do not contact during rotation of the turntable 5. The arm holder 8 includes two pipes 9 moderately bent to an almost right angle, and an arm supporting member 10. The arm supporting member 10 has a shape formed by dividing a doughnut-shaped flat plate into four almost equal parts. One end of each of the two pipes 9 arranged at a predetermined interval is connected to the central portion of the outer periphery of the flat plate. The other end of each pipe 9 is fixed to a rotating shaft 12 which is rotatably supported by a block-shaped holder supporting member 11 provided at the upper end of the subject supporting member 7. The rotating shaft 12 is arranged coaxially with the rotation center 5a of the turntable 5. When the arm holder 8 faces the subject supporting member 7 while the rotation center 5a is interposed between them, the rotating shaft 12 can be locked by a lock mechanism (not shown). At this position, the subject 6 is radiographed. Two grips 13 formed from pipes bent to an almost right angle are provided on the lower surface of the holder supporting member 11 at a predetermined interval.

The procedures of positioning and radiographing the subject 6 in the X-ray CT imaging apparatus shown in FIGS. 1 and 2 will be described next.

The lock mechanism (not shown) is unlocked to release the arm holder 8 at the imaging position. The arm holder 8 is rotated clockwise by about 110° about the rotating shaft 12, as indicated by the alternate long and two short dashed line in FIG. 2. The subject 6 stands upright in tight contact with the subject supporting member 7, raises the arms, and holds the grips 13. In this state, the arm holder 8 is rotated counterclockwise, returned to the imaging position, and fixed by the lock mechanism (not shown). The subject moves the hands off the grips 13 and places the portions from the elbows to forearms on the arm supporting member 10 while putting one upon another. With the above-described procedures, positioning of the subject is ended, and preparations for imaging are completed.

X-rays are irradiated on the basis of X-ray irradiation conditions and preset imaging parameters such as the rotation speed of the turntable 5 simultaneously with rotation of the turntable 5. The radiographic image data of the subject 6 is detected by the X-ray detector 2 at every predetermined angle of the turntable 5 and sequentially transmitted to an image processing unit (not shown). When the turntable 5 rotates by 360° after the start of imaging of the subject 6, the imaging is ended. The image processing unit creates a predetermined tomographic CT image by reconstructing the image data. To change the subject, the subject 6 is made to hold the grips 13 again, and the arm holder 8 is rotated and retracted.

When the arm holder 8 is at the imaging position, the subject may place only the elbows on the arm supporting member 10 while keeping the forearms erect and hold the two pipes 9. The subject may hold the grips 13 or dedicated grips separately provided on the arm holder 8. The shape of the arm supporting member 10 is not limited to the shape of this embodiment. For example, an elongated shape, i.e., a shape formed by dividing a doughnut-shaped flat plate into two almost equal parts may be employed, and the operating angle of rotation/retraction may be increased to 180°. The outer periphery of the arm supporting member need not always have an arc shape unless the X-ray detector 2 and arm supporting member 10 contact during rotation of the turntable 5.

In the above-described arrangement, at least part of the upper arms can be placed on the arm supporting member 10. Hence, the subject need not raise the arms by oneself during imaging. The subject need only rest the upper arms on the arm supporting member and never feels fatigue or pains. Furthermore, a condition with arms retracted from the imaging region can reliably be maintained during imaging.

The arm holder can be rotated and retracted coaxially with the rotation center of the turntable. Since a wide space can be ensured in front of the subject supporting member 10, the subject can easily be changed or positioned or raise the arms. The arm holder is located at the same level as the head of the subject. For this reason, the operability for the radiographer is improved as compared to, e.g., an arrangement which fixes the arms to the subject supporting member by using a fixing belt above the head of the subject. Regardless of whether the arm holder is located at the imaging position or retracting position, a predetermined distance is ensured between the arm holder and the rotation center of the turntable. Hence, the turntable can rotate without contacting the X-ray detector independently of the position of the arm holder, and the operability for the radiographer is improved.

The grips which do not rotate with the arm holder are provided above the head of the subject so that the subject can hold them. Hence, the arm holder can smoothly be operated in setting/retracting to/from the imaging position so the subject feels no fear. In addition, since the subject can also hold the grips during imaging, the subject can feel easy and hold the posture more readily.

Second Embodiment

Figure 3:
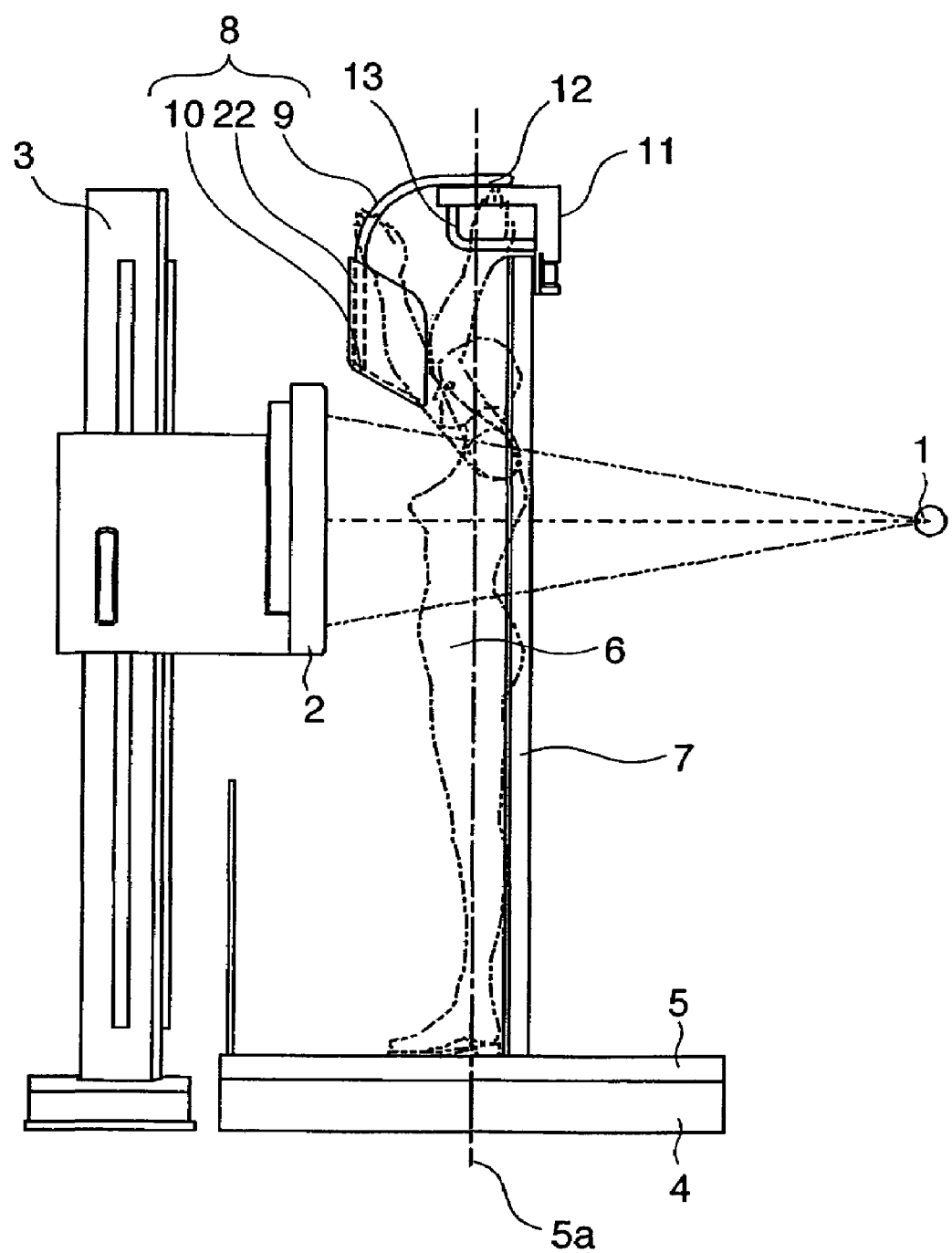
FIG. 3 is a side view showing the schematic arrangement of an X-ray CT imaging apparatus according to the second embodiment of the present invention.

FIG. 3 is a side view showing the schematic arrangement of an X-ray CT imaging apparatus according to the second embodiment of the present invention. The arrangement of the second embodiment will be described with reference to FIG. 3. The X-ray CT imaging apparatus has the same arrangement as in the first embodiment except the arm holder. The same reference numerals as in the first embodiment denote the same members in the second embodiment, and a detailed description thereof will be omitted.

In the second embodiment, a plate which stands upright to a predetermined height and curves along the arc-shaped outer periphery of the flat plate of an arm supporting member 10, i.e., an arm limiting member 22 is integrated with the arm supporting member 10 and forms an arm holder 21 together with two pipes 9.

With this arrangement, the same effect as in the first embodiment can be obtained. In addition, the location of the arms in a direction almost perpendicular to the body axis of the subject can reliably be limited in a space surrounded by a subject supporting member 7 and arm limiting member 22. For this reason, any contact between an X-ray detector 2 and the upper arms of the subject can be prevented, and the safety can be assured during imaging. Furthermore, since the arm limiting member 22 limits the visibility of the subject, the subject never fears that he/she contacts the X-ray detector 2 during imaging, and body motion caused by the fear can be eliminated.

Third Embodiment

Figure 4:
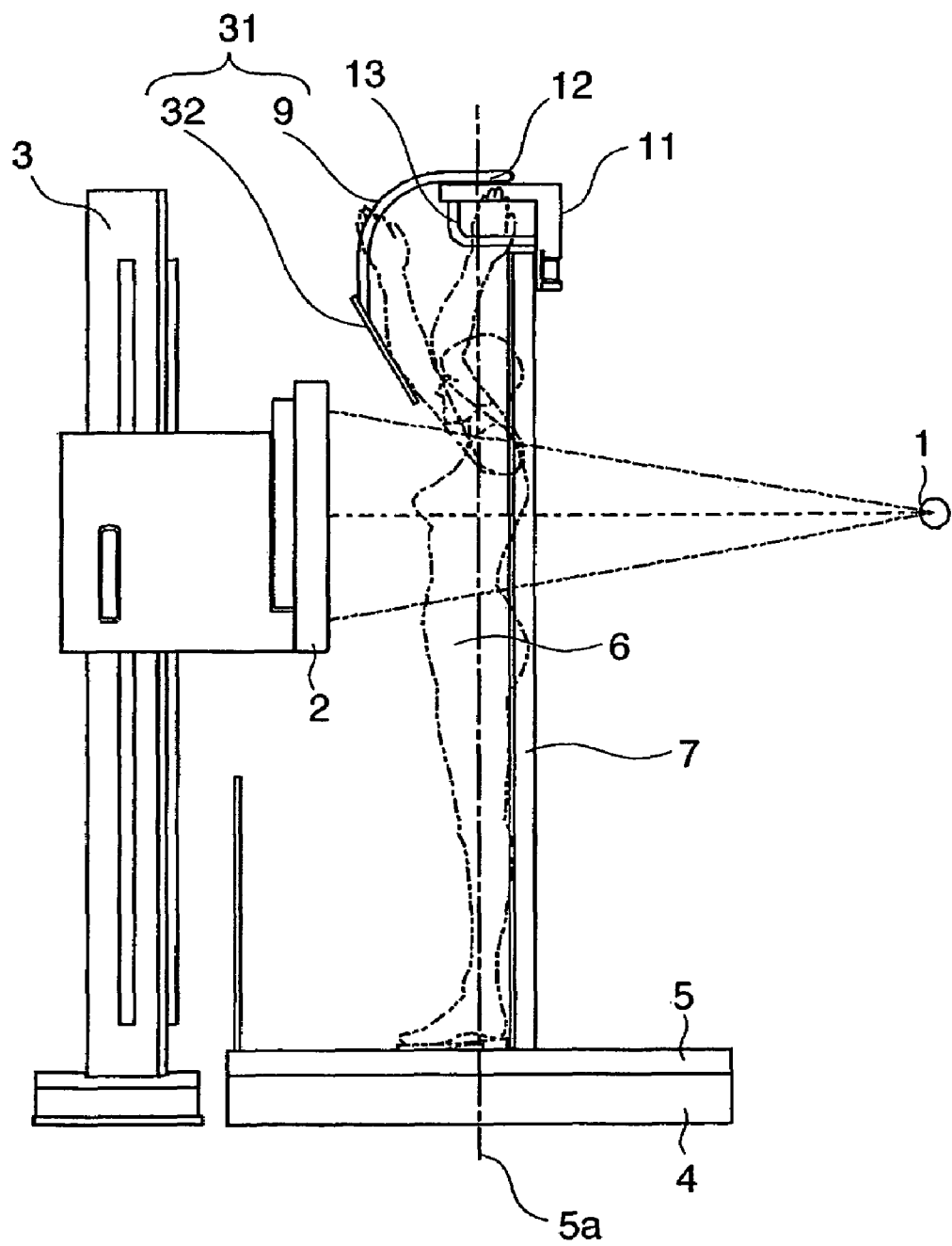
FIG. 4 is a side view showing the schematic arrangement of an X-ray CT imaging apparatus according to the third embodiment of the present invention.

FIG. 4 is a side view showing the schematic arrangement of an X-ray CT imaging apparatus according to the third embodiment of the present invention. The third embodiment is a modification to the above-described second embodiment. The X-ray CT imaging apparatus has the same arrangement as in the first embodiment except the arm holder. The same reference numerals as in the first embodiment denote the same members in the third embodiment, and a detailed description thereof will be omitted.

In the third embodiment, an arm holder 31 includes pipes 9 and an arm supporting member 32, which have the same shapes as in the first embodiment. The arm supporting member 32 has a shape formed by dividing a doughnut-shaped flat plate into four almost equal parts, as in the first embodiment. One end of each of the two pipes 9 arranged at a predetermined interval is connected to the central portion of the outer periphery of the flat plate. The arm supporting member 32, however, tilts by about 45° with respect to the floor surface.

With this arrangement, the function of the arm supporting member 10 of the first embodiment and the function of the arm limiting member 22 of the second embodiment can be implemented by one member. The arm supporting member 32 may stand almost upright with respect to the floor surface, and the entire arm holder 31 may be arranged close to a subject supporting member 7. In this case, the elbows of the subject abut against the arm supporting member 32 so that the upper arms are supported not to drop. Hence, the same effect as described above can be obtained.

Fourth Embodiment

Figure 5:
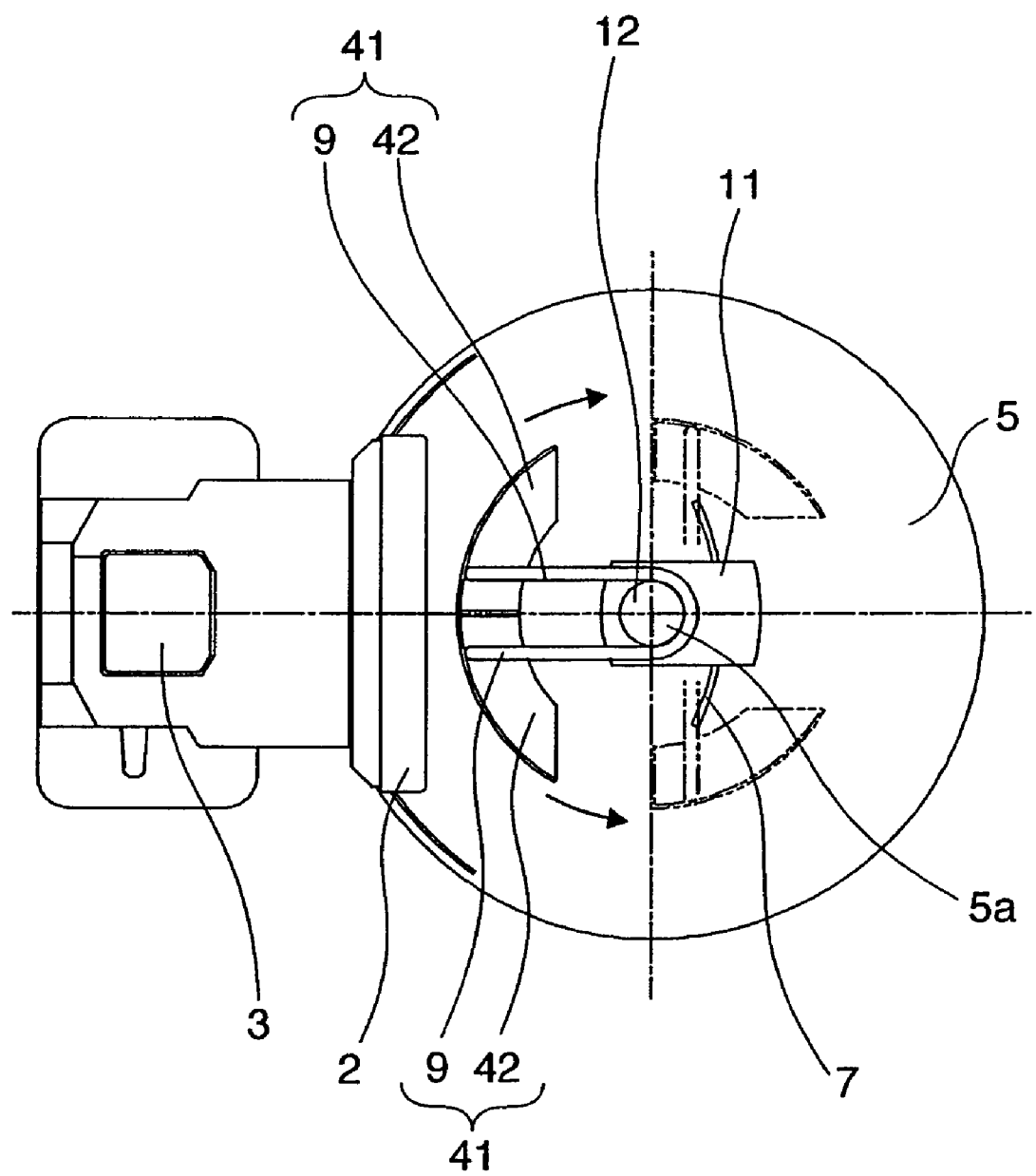
FIG. 5 is a plan view showing the schematic arrangement of an X-ray CT imaging apparatus according to the fourth embodiment of the present invention.

FIG. 5 is a plan view showing the schematic arrangement of an X-ray CT imaging apparatus according to the fourth embodiment of the present invention. The arrangement of the fourth embodiment will be described with reference to FIG. 5. The X-ray CT imaging apparatus has the same arrangement as in the first embodiment except the arm holder. The same reference numerals as in the first embodiment denote the same members in the fourth embodiment, and a detailed description thereof will be omitted.

In the fourth embodiment, arm holders 41 include pipes 9 and arm supporting members 42, which have the same shapes as in the first embodiment. In this embodiment, however, the arm supporting members 42 have a shape formed by dividing the arm supporting member 10 of the first embodiment into two equal parts. The two pipes 9 are connected to the two divided arm supporting members 42. The two pipes 9 can rotate in opposite directions coaxially with a rotation center 5a of the subject.

In positioning a subject 6, a lock mechanism (not shown) is unlocked. The two arm holders 41 at the imaging position are rotated clockwise and counterclockwise, respectively, by about 90°. The subject 6 stands upright in tight contact with a subject supporting member 7, individually places the elbows on the two arm supporting members 42, and erects the forearms. In this state, the two arm holders 41 are rotated in directions in which they move closer to one another, returned to the imaging position, and fixed by the lock mechanism (not shown). The subject places the portions from the elbows to forearms on the arm supporting members 42 while putting one upon another. With the above-described procedures, positioning of the subject is ended, and preparations for imaging are completed. To change the subject, the subject 6 erects the forearms again, and the arm holders 41 are rotated and retracted.

With this arrangement, the same effect as in the first embodiment can be obtained. In addition, since the arm holders 41 can be set/retracted to/from the imaging position while keeping the elbows of the subject placed on the arm supporting members 42, the subject need not hold the raised arms by oneself. Hence, the subject can avoid fatigue and pains more effectively.

Fifth Embodiment

Figure 6:
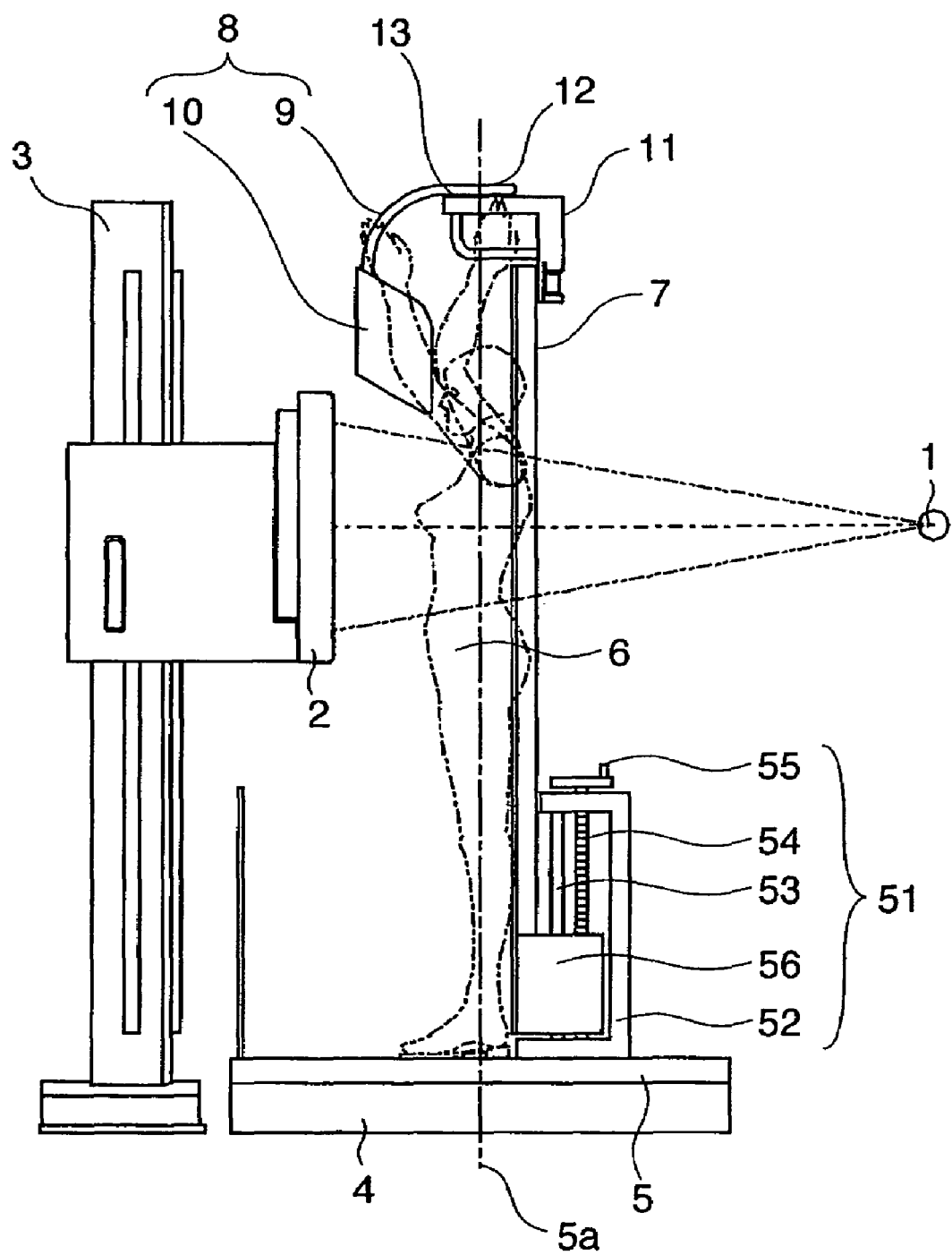
FIG. 6 is a side view showing the schematic arrangement of an X-ray CT imaging apparatus according to the fifth embodiment of the present invention.

FIG. 6 is a side view showing the schematic arrangement of an X-ray CT imaging apparatus according to the fifth embodiment of the present invention. The arrangement of the fifth embodiment will be described with reference to FIG. 6. The same reference numerals as in the first embodiment denote the same members in the fifth embodiment, and a detailed description thereof will be omitted.

In the fifth embodiment, a vertical motion mechanism 51 is provided on the lower and rear side of a subject supporting member 7. The vertical motion mechanism 51 includes a frame 52, guide bar 53, vertical motion screw 54, handle 55, and vertical motion block 56. The frame 52 with a U-shaped section is rotated by 90° and attached to a turntable 5. The guide bar 53 and vertical motion screw 54 standing upright are juxtaposed with their ends being held by the upper and lower portions of the frame 52. The vertical motion screw 54 is supported rotatably with respect to the frame 52. The handle 55 is fixed to the upper end of the vertical motion screw 54. The vertical motion block 56 has two holes. The guide bar 53 and vertical motion screw 54 are fitted in the holes. The guide bar 53 guides the vertical motion block in the vertical direction. A female screw is formed in the hole fitting on the vertical motion screw 54 and threadably engages with a male screw formed almost along the whole length of the vertical motion screw 54. The lower end of the subject supporting member 7 is connected to the vertical motion block 56. The vertical motion block 56 moves in the vertical direction interlockingly with rotation of the handle 55. Hence, an arm holder 8 connected to the subject supporting member 7 can be adjusted to a desired level.

With this arrangement, the operability for the radiographer is improved as compared to an arrangement which adjusts the arm holder 8 to a desired level by moving a holder supporting member 11 arranged above the head of the subject vertically with respect to the subject supporting member 7. If the subject is especially tall, and the radiographer is short, the operation is sometimes impossible. However, since the operation spot is located at the low position, the photographer can properly operate the apparatus and need not adjust the position while supporting the arm holder not to drop.

Even after positioning of the subject and its arms is ended, and preparations for imaging are completed, the level of the arms can easily finely be adjusted. If the subject has difficulty in raising the arms or holding the raised arms by oneself, positioning is done first at a relatively low arm position. After that, the arm holder is adjusted to a desired level. Hence, the load on the subject is reduced.

Sixth Embodiment

Figure 7:
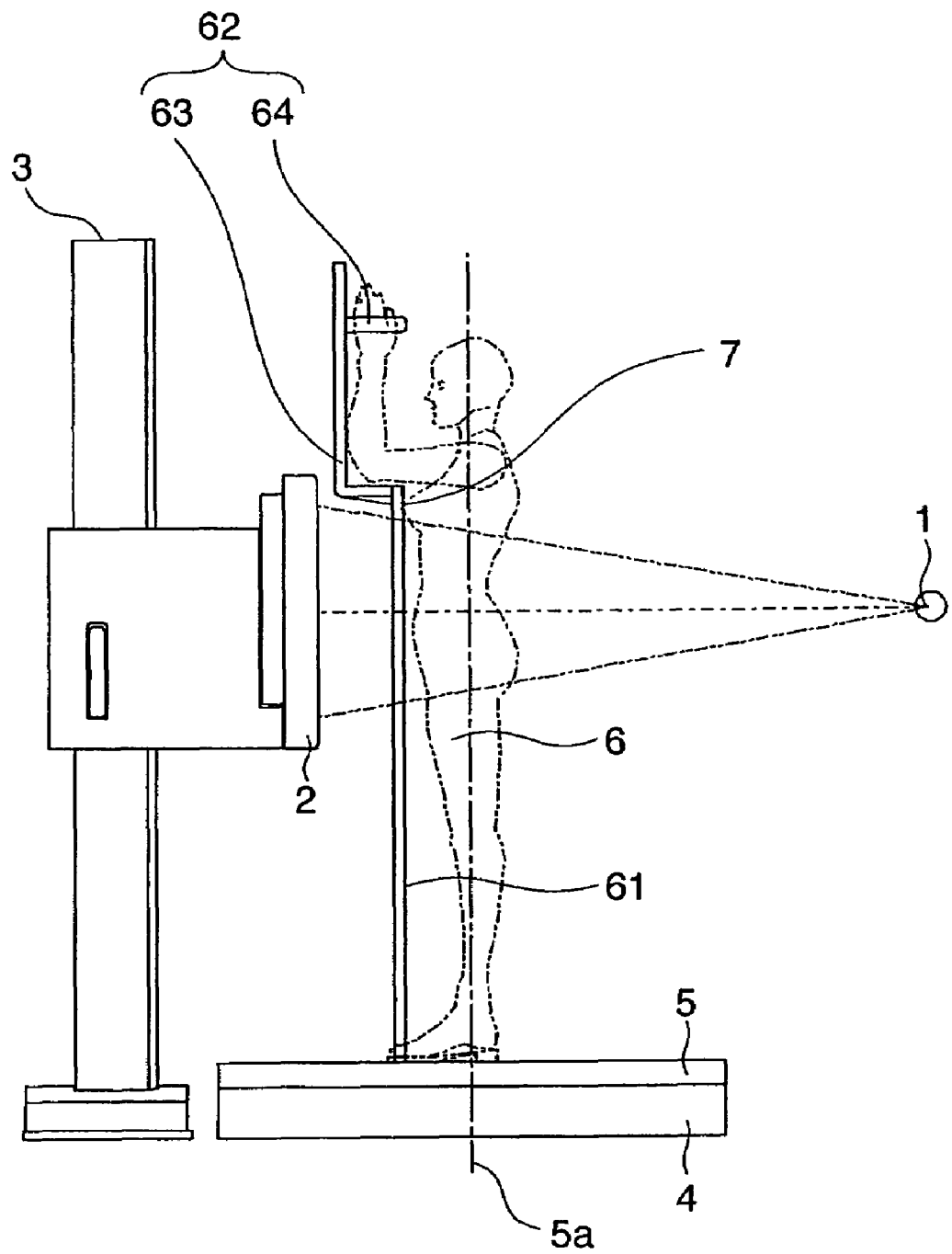
FIG. 7 is a side view showing the schematic arrangement of an X-ray CT imaging apparatus according to the sixth embodiment of the present invention.

FIG. 7 is a side view showing the schematic arrangement of an X-ray CT imaging apparatus according to the sixth embodiment of the present invention. The arrangement of the sixth embodiment will be described with reference to FIG. 7. The same reference numerals as in the first embodiment denote the same members in the sixth embodiment, and a detailed description thereof will be omitted.

In the sixth embodiment, a plate-shaped subject supporting member 61 is provided on a turntable 5. The subject supporting member 61 arranges a subject 6 standing upright near a rotation center 5a and supports the front side of the subject 6 along the body axis. An arm holder 62 to arrange and support the arms of the subject 6 at a desired position is arranged above the subject supporting member 61. The arm holder 62 includes an arm supporting member 63 and grips 64. The arm supporting member 63 includes two flat plates which have almost the same width as that of the subject supporting member 61 and are integrated by making the ends butt against each other at an almost right angle. The two grips 64 have a round rod shape and are fixed at a predetermined interval vertically on the upright plate of the arm supporting member 63. The arm holder 62 is connected to the subject supporting member 61 through a holder supporting member 65 provided at the upper end of the subject supporting member 61.

In positioning the subject 6, the subject 6 need only stand upright in tight contact with the subject supporting member 61, raise the arms, and place the elbows on the horizontal plate of the arm supporting member 63 while holding the grips 64.

With the above-described arrangement, the same effect as in the first to third embodiments can be obtained. In addition, since the arm holder need not be retracted in changing the subject, the operability for the radiographer is further improved.

Seventh Embodiment

Figure 8:
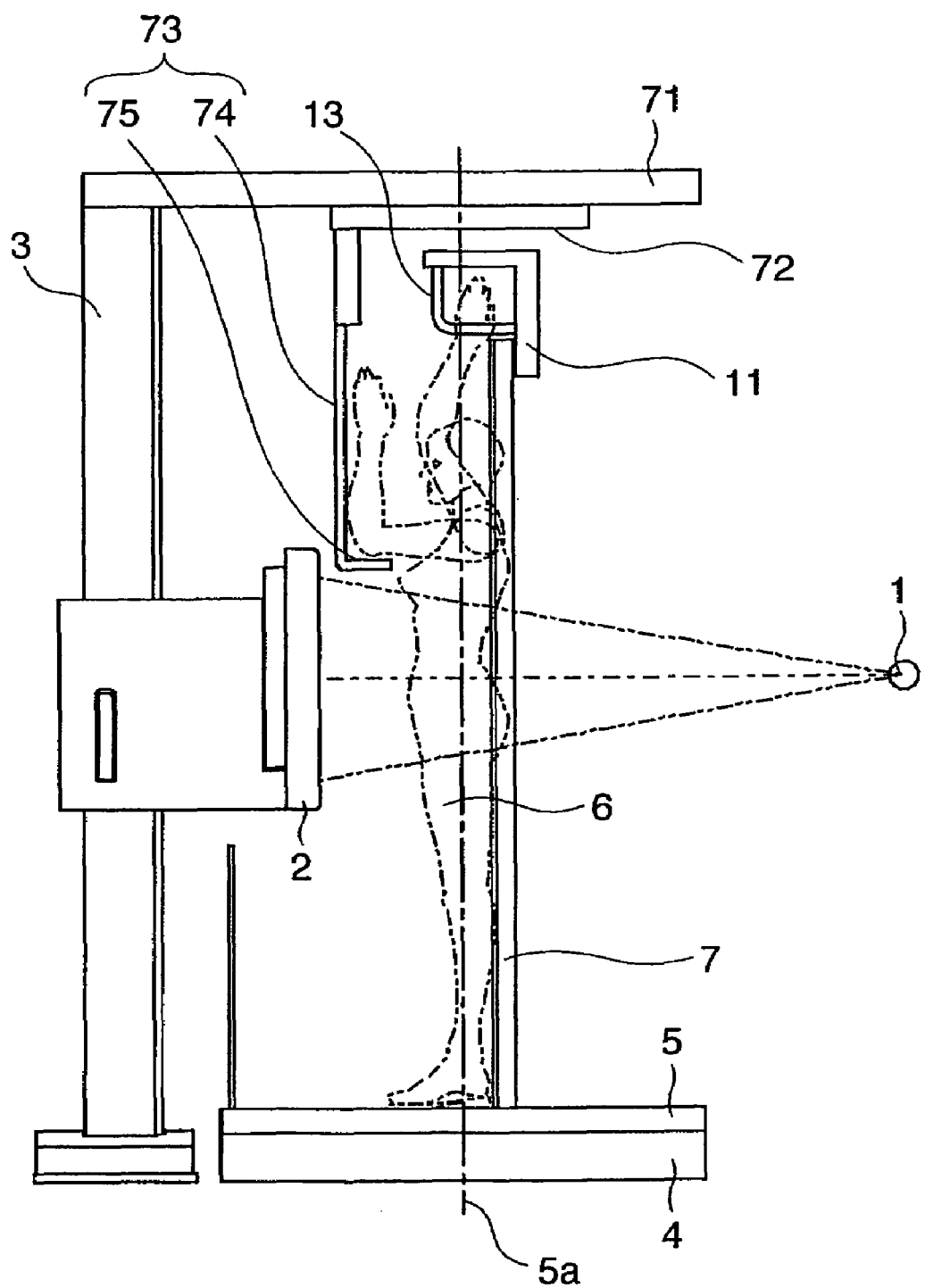
FIG. 8 is a side view showing the schematic arrangement of an X-ray CT imaging apparatus according to the seventh embodiment of the present invention.

FIG. 8 is a side view showing the schematic arrangement of an X-ray CT imaging apparatus according to the seventh embodiment of the present invention. The arrangement of the seventh embodiment will be described with reference to FIG. 8. The same reference numerals as in the first embodiment denote the same members in the seventh embodiment, and a detailed description thereof will be omitted.

In the seventh embodiment, a holder supporting member 71 having almost the same area as that of a turntable 5 is provided at the upper end of a supporting member 3 to support an X-ray detector 2 and faces the turntable 5. The holder supporting member 71 rotatably supports a rotating shaft 72. The rotating shaft 72 is arranged coaxially with a rotation center 5a of the turntable 5. An arm holder 73 is fixed to the rotating shaft 72 while being spaced apart from the rotation center 5a by a predetermined distance. The arm holder 73 includes a connecting plate 74 and arm supporting member 75. The connecting plate 74 is arranged upright and includes two flat plates which are integrated by making the ends butt against each other at an almost right angle, as in the sixth embodiment. The arm supporting member 75 is arranged horizontally. The connecting plate 74 is fixed to the rotating shaft 72.

In positioning a subject 6, the subject 6 need only stand upright in tight contact with a subject supporting member 7, raise the arms, and place the elbows on the horizontal plate of the arm supporting member 75. With the above-described arrangement, the same effect as in the sixth embodiment can be obtained.

Eighth Embodiment

Figure 9:
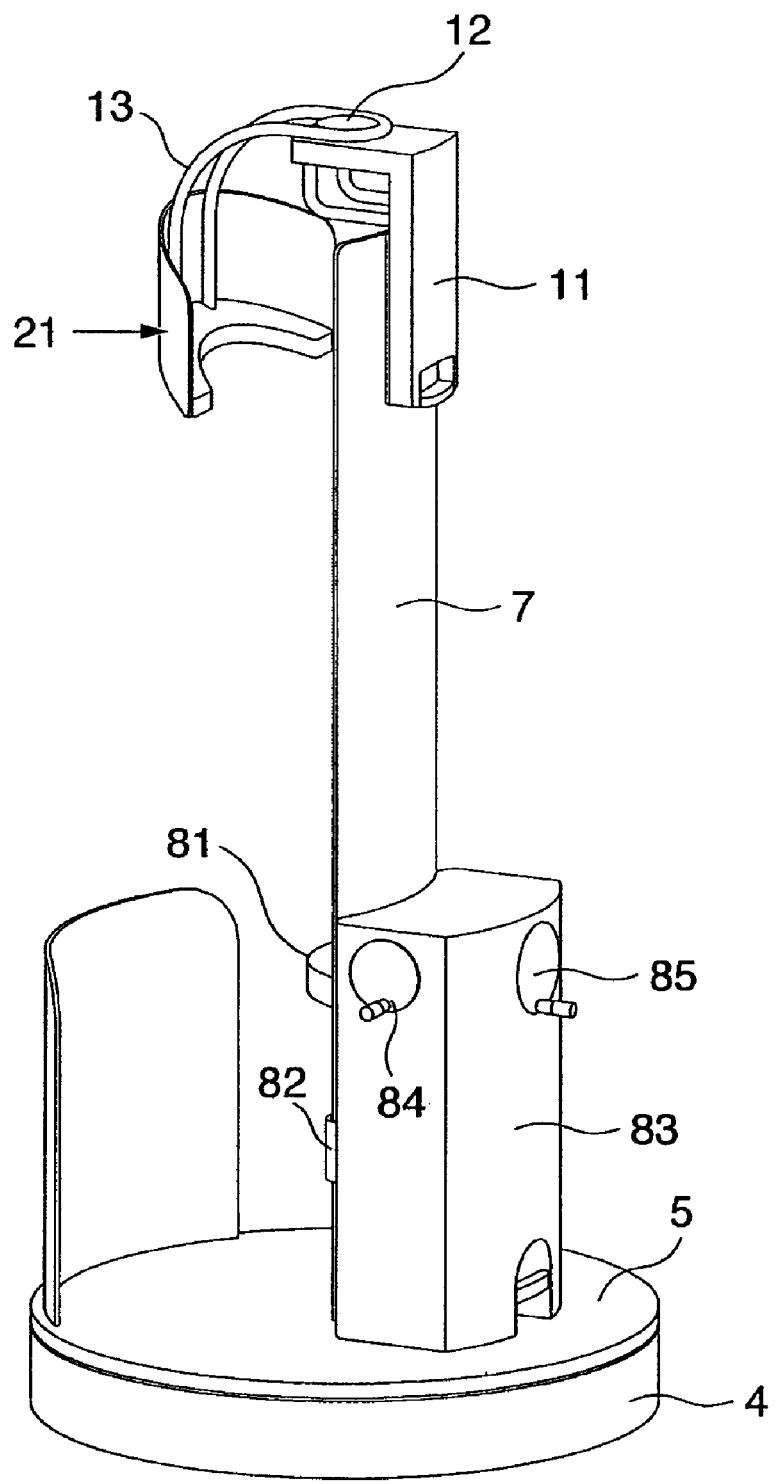
FIG. 9 is a perspective view showing the schematic arrangement of an X-ray CT imaging table according to the eighth embodiment of the present invention.
Figure 11:
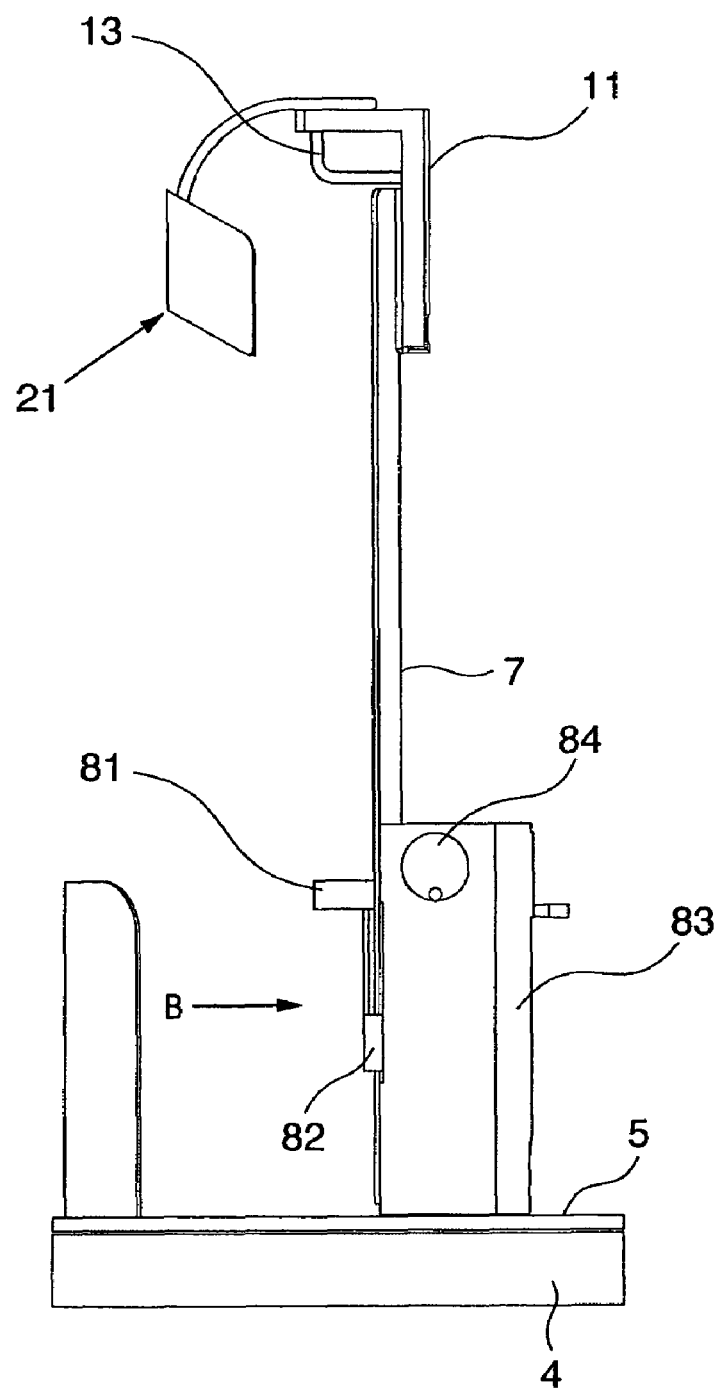
FIG. 11 is a right side view of the apparatus in FIG. 9.
Figure 12:
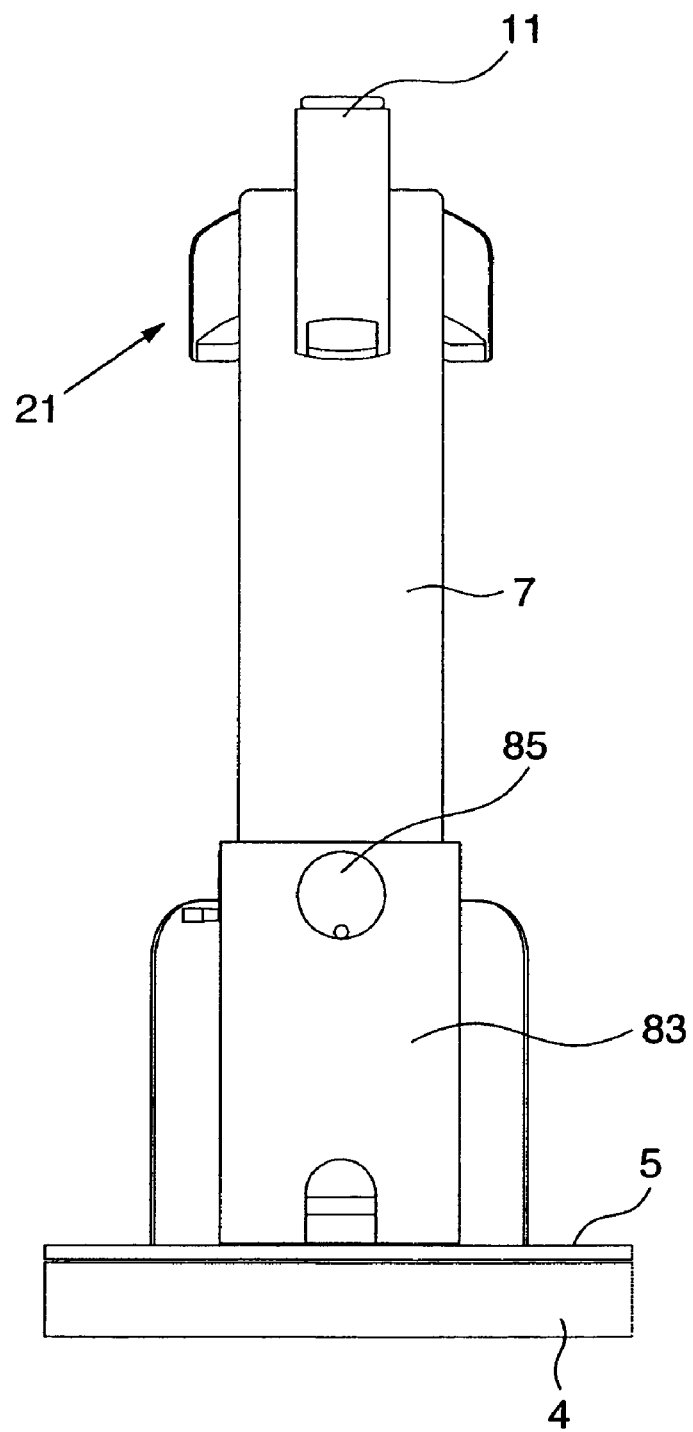
FIG. 12 is a rear view of the apparatus in FIG. 9.
Figure 13:
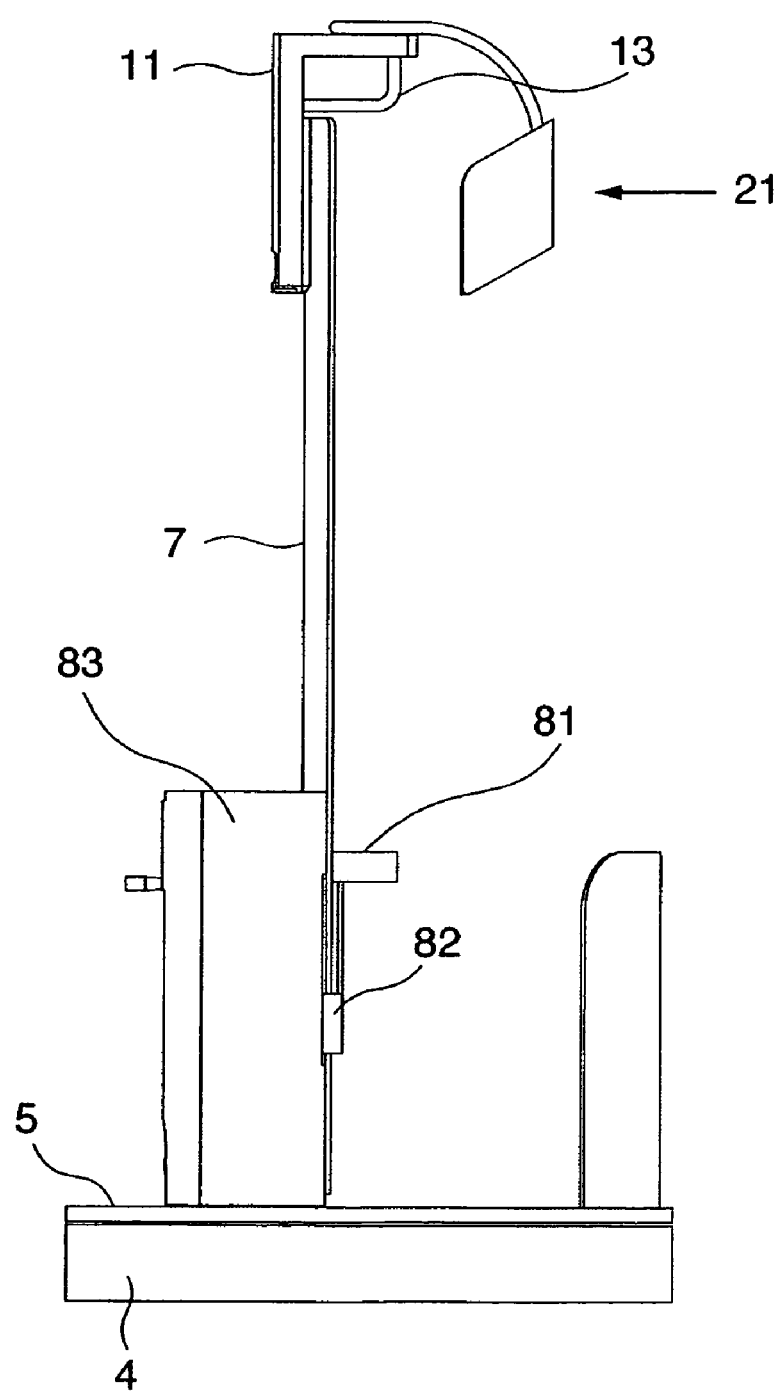
FIG. 13 is a left side view of the apparatus in FIG. 9.
Figure 14:
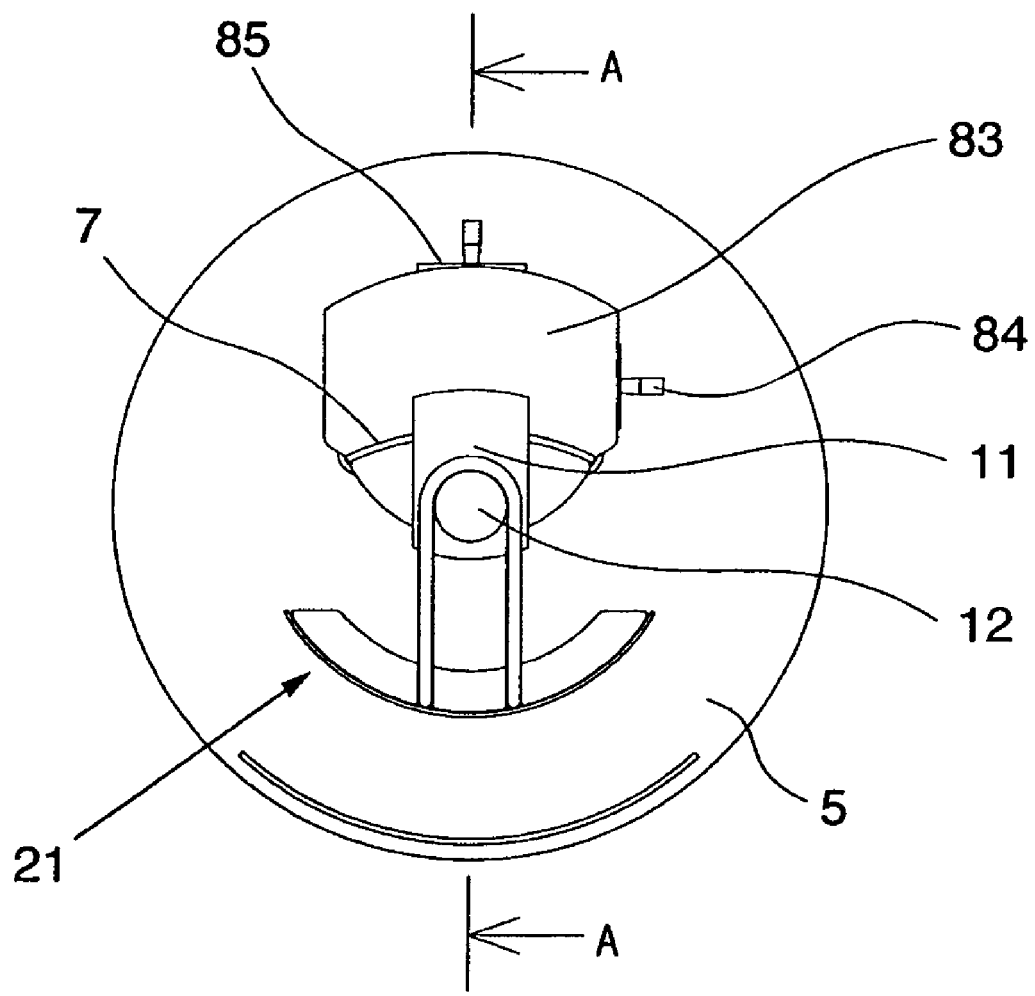
FIG. 14 is a plan view of the apparatus in FIG. 9.
Figure 15:
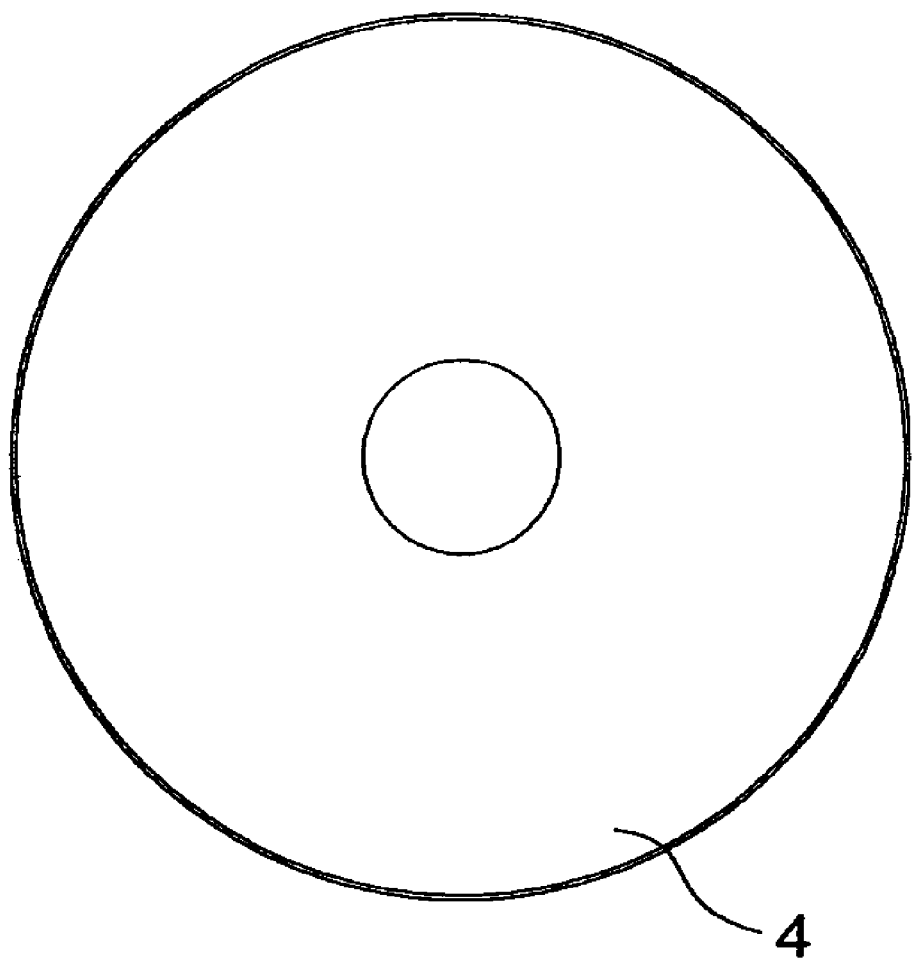
FIG. 15 is a bottom view of the apparatus in FIG. 9.
Figure 16:
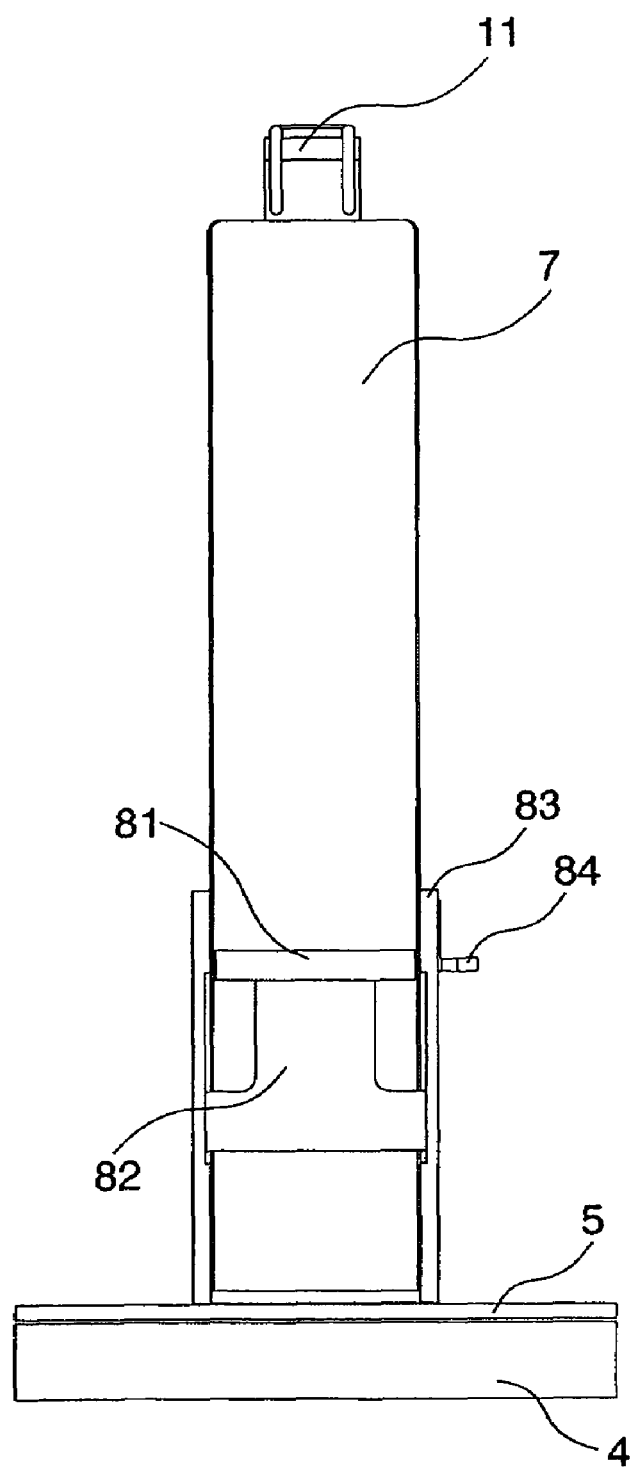
FIG. 16 is a view of the apparatus in FIG. 11 viewed from the direction of an arrow B.
Figure 17:
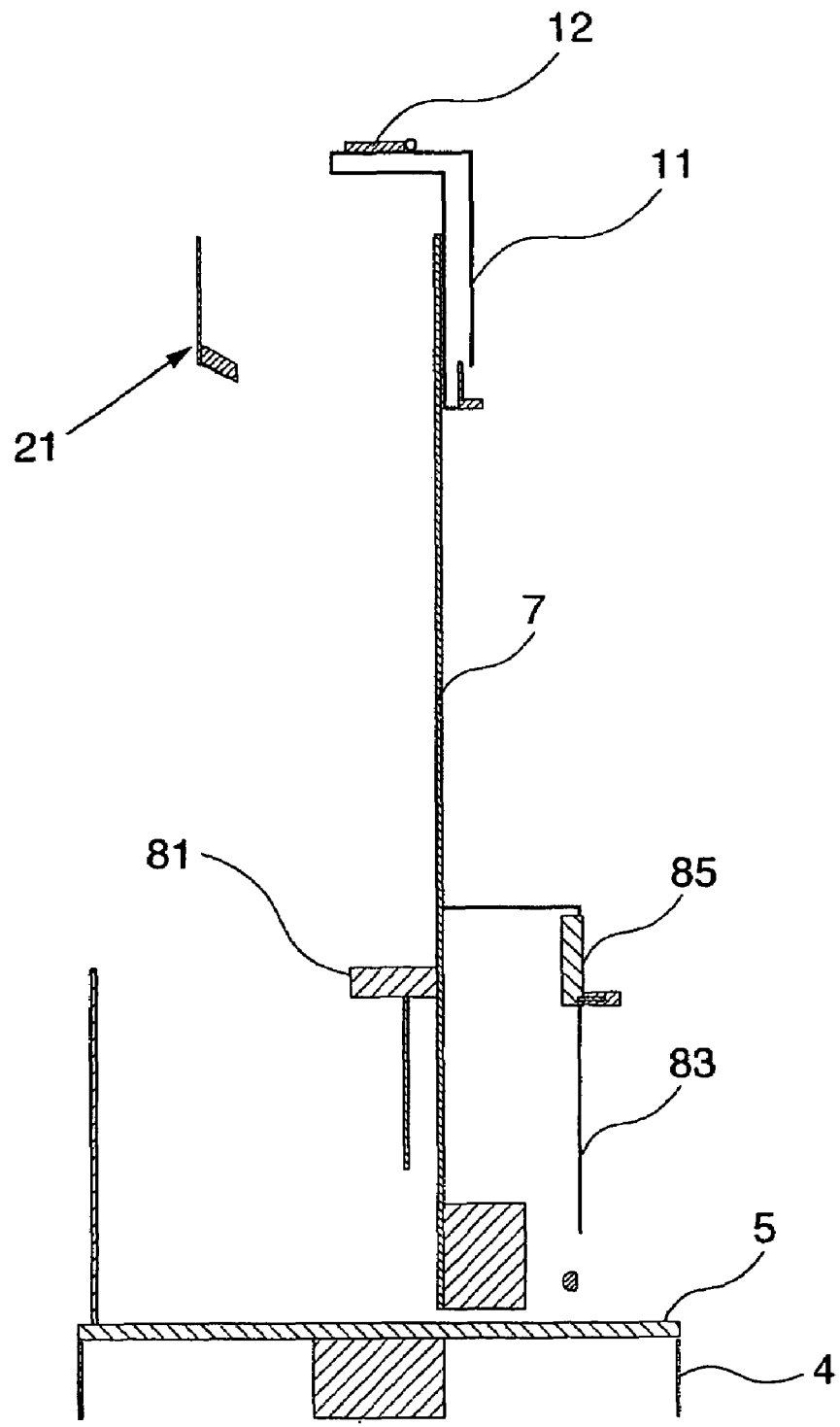
FIG. 17 is a sectional view taken along a line A-A in FIG. 14.

FIG. 9 is a perspective view showing the schematic arrangement of the radiographic imaging table of an X-ray CT imaging apparatus according to the eighth embodiment of the present invention. FIG. 10 is a front view of the apparatus in FIG. 9. FIG. 11 is a right side view of the apparatus in FIG. 9. FIG. 12 is a rear view of the apparatus in FIG. 9. FIG. 13 is a left side view of the apparatus in FIG. 9. FIG. 14 is a plan view of the apparatus in FIG. 9. FIG. 15 is a bottom view of the apparatus in FIG. 9. FIG. 16 is a view of the apparatus in FIG. 11 viewed from the direction of an arrow B. FIG. 17 is a sectional view taken along a line A-A in FIG. 14 in which no internal arrangement is illustrated. The arrangement of the eighth embodiment will be described with reference to FIGS. 9 to 17. The same reference numerals as in the second embodiment denote the same members in the eighth embodiment, and a detailed description thereof will be omitted.

A vertical motion mechanism (not shown) to adjust a subject supporting member 7 to a desired level is provided on the lower and rear side of the subject supporting member 7, as in the fifth embodiment. Another vertical motion mechanism (not shown) to adjust a chair 81 for holding the subject in a sitting position to a desired level is also provided on the lower and rear side of the subject supporting member 7. The chair 81 is arranged on the front side of the subject supporting member 7 and fixed to a connecting plate 82. The connecting plate 82 is connected to the vertical motion mechanism of the chair 81 from the outside of the two side surfaces of the subject supporting member 7. A cover 83 is arranged to cover the two vertical motion mechanisms.

Handles 84 and 85 are connected to the vertical motion mechanisms of the subject supporting member 7 and chair 81 and exposed from the cover 83. The subject supporting member 7 and chair 81 can move in the vertical direction interlockingly with rotation of the handles.

With the above-described arrangement, the same effect as in the fifth embodiment can be obtained. In addition, since the subject can sit, the load on the subject is reduced.

[Modification]

The preferred embodiments of the present invention have been described above. The present invention is not limited to these embodiments, and various changes and modifications can be made within the spirit and scope of the present invention.

For example, the chair to hold the subject in a sitting position may be provided not on the subject supporting member but on the turntable. Imaging may be done while integrally rotating the imaging system including the X-ray tube and X-ray detector about the subject instead of rotating the subject. The present invention can also be applied even when the holder supporting member 71 of the seventh embodiment is fixed not to the supporting member 3 but to the ceiling of the imaging chamber where the X-ray CT imaging apparatus is installed.

As many apparently widely different embodiments of the present invention can be made without departing from the spirit and scope thereof, it is to be understood that the invention is not limited to the specific embodiments thereof except as defined in the appended claims.

This application claims the benefit of Japanese Application No. 2005-075557, filed Mar. 16, 2005, which is hereby incorporated by reference herein in its entirety.

What is claimed is:

1. A radiographic imaging apparatus which includes an imaging system having a radiation source to irradiate a subject with radiation and a radiation detector to detect the radiation irradiated from the radiation source; and a radiographic imaging table to arrange the subject within the imaging system, comprising:
    a subject supporting member adapted to support the subject in a direction of the body axis;
    an arm holder on which upward arms of the subject in an upright posture are placed; and
    a holder supporting member which supports said arm holder and is provided at the upper end of the subject supporting member.

2. The apparatus according to claim 1, further comprising means for relatively rotating the imaging system and the subject on the radiographic imaging table.

3. The apparatus according to claim 1, wherein said arm holder has an arm supporting member which supports the arms of the subject from below or sides.

4. The apparatus according to claim 1, wherein said arm holder has an arm limiting member which limits positions of the arms in a direction substantially perpendicular to a body axis of the subject.

5. The apparatus according to claim 1, further comprising a rotating shaft which rotatably supports said arm holder through said holder supporting member, said rotating shaft being arranged substantially coaxially with a rotation center about which one of the subject and the imaging system rotates.

6. The apparatus according to claim 5, wherein said arm holder is divided to left and right parts with respect to the body axis of the subject, and said left and right parts are rotatable in opposite directions.

7. The apparatus according to claim 1, further comprising a grip provided above said arm holder to be held by the subject.

8. The apparatus according to claim 7, wherein said grip includes at least one of a first grip provided on one of said holder supporting member and a subject supporting member to support the subject in a direction of the body axis and a second grip provided on said arm holder.

9. The apparatus according to claim 1, wherein
    said arm holder is fixed to the subject supporting member to support the subject in the direction of the body axis, and
    the apparatus further comprises a guide member which vertically moves the subject supporting member with respect to the subject.

10. The apparatus according to claim 1, wherein said holder supporting member is connected to one of the subject supporting member to support the subject in the direction of the body axis, a detector supporting member to support the radiation detector, and an upper portion of an imaging chamber.

11. A radiographic imaging table on which a subject is arranged within an imaging system including a radiation source to irradiate the subject with radiation and a radiation detector to detect the radiation irradiated from the radiation source, comprising:
    a subject supporting member to support the subject in a direction of the body axis;
    an arm holder on which upward arms of the subject in an upright posture are placed; and
    a holder supporting member which supports said arm holder and is provided at the upper end of the subject supporting member.

12. The table according to claim 11, further comprising means for relatively rotating the subject and the imaging system.

13. The table according to claim 11, wherein said arm holder has an arm supporting member which supports the arms of the subject from below or sides.

14. The table according to claim 11, wherein said arm holder has an arm limiting member which limits positions of the arms in a direction substantially perpendicular to a body axis of the subject.

15. The table according to claim 11, further comprising a rotating shaft which rotatably supports said arm holder through said holder supporting member, said rotating shaft being arranged substantially coaxially with a rotation center about which one of the subject and the imaging system rotates.

16. The table according to claim 15, wherein said arm holder is divided to left and right parts with respect to the body axis of the subject, and said left and right parts are rotatable in opposite directions.

17. The table according to claim 11, further comprising a grip provided above said arm holder to be held by the subject.

18. The table according to claim 17, wherein said grip includes at least one of a first grip provided on one of said holder supporting member and a subject supporting member to support the subject in a direction of the body axis and a second grip provided on said arm holder.

19. The table according to claim 11, wherein
    said arm holder is fixed to the subject supporting member to support the subject in the direction of the body axis, and the table further comprises a guide member which vertically moves the subject supporting member with respect to the subject.

20. The table according to claim 11, wherein said holder supporting member is connected to one of the subject supporting member to support the subject in the direction of the body axis, a detector supporting member to support the radiation detector, and an upper portion of an imaging chamber.

* * * * *